United States Patent [19]

Mackool

[11] Patent Number: 4,693,716

[45] Date of Patent: Sep. 15, 1987

[54] MULTIPARTITE INTRAOCULAR LENS

[76] Inventor: Richard J. Mackool, 31-27 41st St., Astoria, N.Y. 11103

[21] Appl. No.: 643,030

[22] Filed: Aug. 21, 1984

[51] Int. Cl.[4] ............................ A61F 1/16; A61F 3/13
[52] U.S. Cl. ....................................................... 623/6
[58] Field of Search ............................................ 623/6

[56] References Cited

U.S. PATENT DOCUMENTS

| 4,268,921 | 5/1981 | Kelman | 623/6 |
| 4,296,501 | 10/1981 | Kelman | 623/6 |
| 4,451,938 | 6/1984 | Kelman | 623/6 |

Primary Examiner—V. Millin
Attorney, Agent, or Firm—Cobrin & Godsberg

[57] ABSTRACT

An intracular lens implant including a lens centered on a lens axis and the lens body having a plurality of separate sections to permit initial separate introduction of the respective sections into the eyeball through an incision smaller than that which would be needed for the introduction of the complete lens body. Means are provided for holding the assembled lens body in a predetermined position in the eye. One of the sections is substantially C-shaped and another is a substantially circular section, with each of these sections having surfaces which face one another, and means are provided to hold the sections relative to each other.

11 Claims, 9 Drawing Figures

U.S. Patent   Sep. 15, 1987   4,693,716
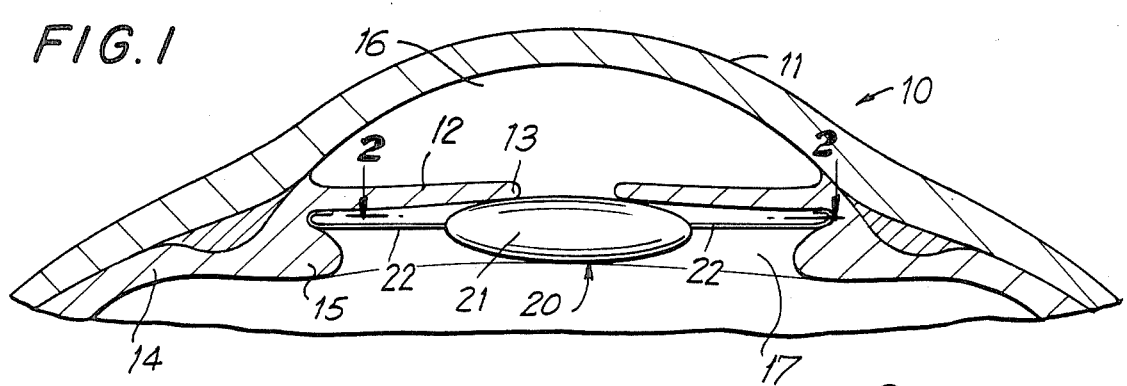
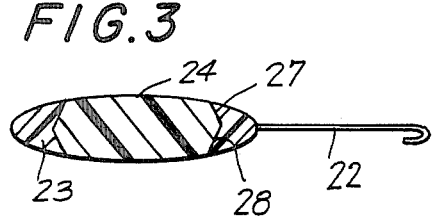
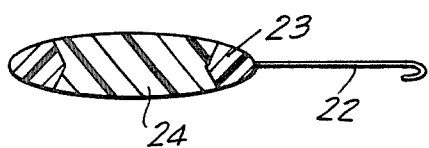
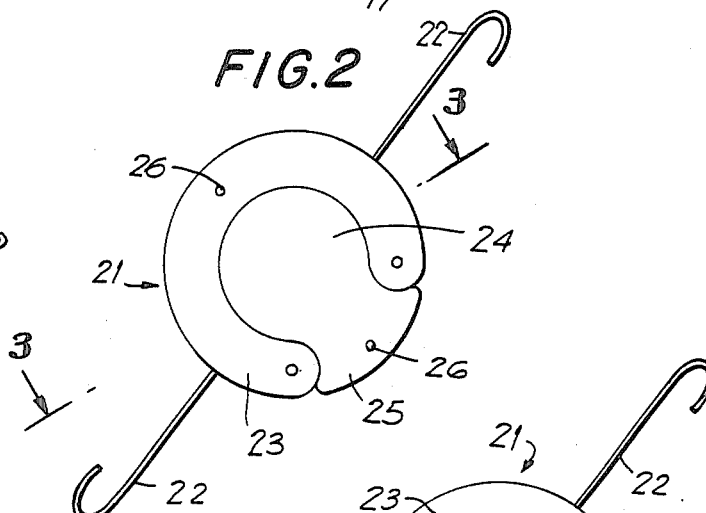
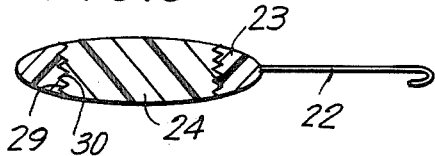
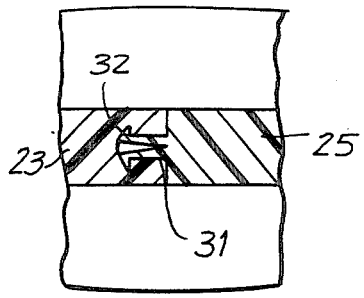
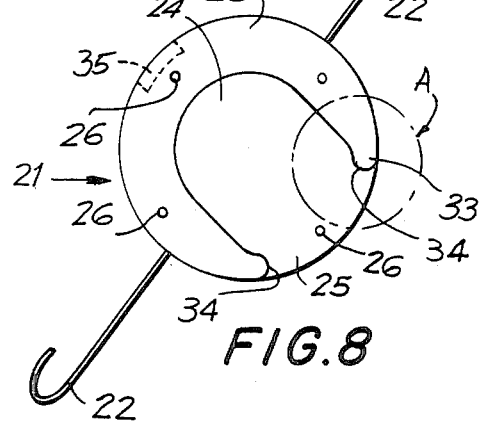

MULTIPARTITE INTRAOCULAR LENS

BACKGROUND OF THE INVENTION

The present invention relates to artificial implants for human bodies in general, and more particularly to intraocular lens implants to be introduced into human eyes after the natural lens has been removed.

There are already known various constructions of intraocular lens implants and ways of mounting the same in the eyeball, either in the anterior chamber or in the posterior chamber. Such implants are shown, for instance, in U.S. Pat. Nos. 3,991,426; 4,053,953; 4,056,855; 4,134,160; 4,159,546; 4,268,921; 4,296,501; 4,338,687; 4,343,050; and 4,403,354. Such implants are held in position in the eye by either being secured to the iris or its stroma, or by being equipped with holding means which brace themselves against the internal surfaces bounding a part of the respective anterior or posterior chamber of the eye in which the lens is to be mounted.

Experience with the heretofore known intraocular lens implants has shown, however, that the incision that has to be made into the eye in order to be able to introduce any one of the known implants into the respective chamber must be relatively long. It is also known that, the longer the incision, the longer it takes for it to heal, the greater the danger of rupture of the incision postoperatively, and the greater is the danger that scar tissue which forms during the healing process will interfere with vision. Moreover, the tissue of the iris is incapable of healing if torn or otherwise damaged so that, if the lens is to be introduced into the posterior chamber through the pupil of the iris which is artificially dilated during this operation by the use of appropriate drugs, the relatively large size of the lens implants according to the prior art could occasionally result in permanent damage to the iris. Yet, heretofore, there was not proposed any approach which would avoid these problems, even though the existence of such problems has been recognized by those skilled in the art of eye surgery.

SUMMARY OF THE INVENTION

Accordingly, it is a general object of the present invention to avoid the disadvantages of the prior art.

More particularly, it is an object of the present invention to provide an intraocular lens implant which does not possess the disadvantages of the previously known intraocular implants.

Still another object of the present invention is so to design the intraocular lens implant as to reduce the size of the incision which is to be made in the eyeball in order to be able to introduce the lens implant into the respective chamber of the eye, and to minimize the possibility of damage to the iris, if not eliminate such danger altogether.

It is a concomitant object of the present invention so to construct the intraocular lens implant as to be relatively simple in construction, inexpensive to manufacture, easy to use, and reliable in operation nevertheless.

In pursuance of these objects and others which will become apparent hereafter, one feature of the present invention resides in an intraocular lens implant which comprises a lens body centered on a lens axis and extending along a plane normal to the lens axis, the lens body including a plurality of separate sections each of which has at least one dimension as considered along the lens plane which is a fraction of the diameter of the lens body to permit initial separate introduction of the respective sections into the eyeball through an incision smaller than that which would be needed for the introduction of the complete lens body, followed by subsequent assembly of the sections in the eyeball into the lens body; and means for holding the unassembled and then the assembled lens body in a predetermined position in the eyeball.

A particular advantage of the construction described so far is that the individual sections can be introduced into the interior of the eye through a much smaller incision than heretofore possible, the size of the incision being determined by the configuration of the sections and, to a lesser extent, by the size of any instruments which are needed for assembling and positioning the lens implant in the interior of the eyeball. In this respect, it is particularly advantageous when one of these sections is a substantially C-shaped peripheral section and another one of the sections is a substantially circular central section which is at least partially circumferentially surrounded by the peripheral section in the assembled condition of the lens body. It is further advantageous when at least the peripheral section is resiliently yieldable, and when the peripheral section extends along an arc exceeding 180 degrees to permit introduction of the central section thereinto upon resilient spreading thereof and to retain the central section therein upon discontinuance of the spreading action.

A particularly advantageous construction of the lens implant according to the present invention is obtained when the peripheral and central sections have respective internal and external surfaces which face one another in the assembled condition of the lens body, one of these surfaces being provided with at least one projection whereas the other of these surfaces has at least one recess which receives the projection in the assembled condition of the lens body to hold the central section in a predetermined position relative to the peripheral section. In this respect, it is especially advantageous when the projection is configured as a substantially circumferentially extending rib, and when the recess is configurated as a substantially circumferentially extending groove.

In accordance with a currently preferred aspect of the present invention, the peripheral section extends over an arc only slightly exceeding 180 degrees, and the lens body further includes an additional peripheral section which is separate from and is substantially complementary to the aforementioned peripheral section. In this connection, it is advantageous when the additional peripheral section is integral with the central section. However, it is also advantageous and contemplated by the present invention for the additional peripheral section to be separate from the central section as well. In this case, there is provided means for connecting the additional peripheral section to the remainder of the lens body. Such connecting means advantageously includes cooperating male and female connecting formations provided on the respective sections and engaging one another with a snap action. As a matter of fact, such connecting portions can also be used, in accordance with another facet of the present invention, for connecting the central section to the peripheral section.

When the additional peripheral section is integral with the central section, it is further advantageous when there are provided respective complementary bulges and depressions on the end portions of the peripheral section which accommodate the additional peripheral section between themselves, and on the latter. The bulges are preferably formed on the peripheral section to provide a smooth transition at the outer periphery of the respective end portion. A peripheral, preferably dove-tailshaped, engaging opening can be provided on the periphery of the respective section, especially the peripheral section, for engagement by a handling tool.

The novel features which are considered as characteristic of the invention are set forth in particular in the appended claims. The improved intraocular lens implant itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 1 is a considerably enlarged vertical sectional view through an eye having an intraocular lens implant according to the present invention accommodated and supported in its posterior chamber;

FIG. 2 is a horizontal plane view of the intraocular lens implant of the present invention alone, taken on line 2—2 of FIG. 1;

FIG. 3 is a vertical cross-sectional view through the intraocular lens implant, taken on line 3—3 of a FIG. 2;

FIG. 4 is a view similar to FIG. 3 but of a modified construction;

FIG. 5 is a view similar to that of FIG. 3 but showing a further modification of the intraocular lens implant;

FIG. 6 is a view similar to FIG. 2 but showing a modified construction of the intraocular lens implant including three sections;

FIG. 7 is a further enlarged vertical section view of a detail taken on a line 7—7 of FIG. 6;

FIG. 8 is a view similar to that of FIG. 2 but showing a modified configuration; and FIG. 9 is a fragmentary view corresponding to a detail A of FIG. 8 but showing a further modification of the configuration.

DETAILED DESCRIPTION OF THE PREFERRED EMBODIMENTS

With the increasing average age of the population, the percentage of people who suffer from cataracts also increases. The development of a cataract (clouding of the normal human lens) invariably resulted in ultimate blindness of the affected eye. There was developed a procedure for the removal of the natural lens which had been affected by the opacification process, resulting in the loss of most if not all of its light transmissivity. After this procedure, the incision made in the eyeball for the removal of the natural lens was closed, and eventually, after the healing of the tissue, the patient was fitted with an eyeglass lens or a contact lens which, to a degree, compensated for the loss of the natural lens. However, since such artificial lenses are situated at the outside of the eyeball, that is, at a frontward distance from the lens plane of the natural lens, the image projected thereby onto the retina was different from that projected by the natural lens (i.e. larger), so that the patient had to learn to compensate for this difference. In more recent times, this drawback was eliminated by the use of lens implants.

Referring now to the drawing in detail, and first to FIG. 1 thereof, it may be seen that the reference numeral 10 has been used therein to identify an eye. The eye 10 includes a cornea 11, an iris 12, a stroma 13, a choroid 14 and a ciliary process 15. The cornea 11 and the iris 12 bound an anterior chamber 16, whereas a posterior chamber 17 is situated rearwardly of the iris 12. The stroma 13 and the ciliary process 15 together bound the posterior chamber 17.

An artificial intraocular lens implant, indicated generally at 20, is shown to be accommodated in the posterior chamber 17; however, it will be appreciated that the lens implant 20 could also be located in the anterior chamber 16, if so desired. The lens implant 20 includes a lens body 21, and a plurality of elongated supporting elements 22 which support the lens body 21 in the posterior chamber 17 engaging the surface bounding the latter.

As shown in FIG. 2, the lens body 21 consists, in accordance with the present invention, of a plurality of sections, namely, in this instance, of a peripheral section 23 and a central section 24. The peripheral section 23 extends along a substantially C-shaped arc or course, the arc thereof covering slightly more than 180 degrees. The central section 24, on the other hand, may be of a generally circular configuration but, as shown in FIG. 2, it may be provided with an additional peripheral section 25 which is integral therewith and is substantially complementary to the peripheral section 23. The sections 23 snd 24 can be assembled with one another in the interior of the eye 10 by spreading the peripheral section 23 and by introducing the central section 24 into the space bounded by the peripheral section 23 through the thus enlarged gap between the end portion of the peripheral section 23. Of course, during this assembling operation, the additional peripheral section 25, if present, will be so positioned as to enter the above-mentioned gap and to substantially fill the same once the spreading of the peripheral section 23 is terminated. To facilitate the handling of the sections 23 and 24 and manipulation therewith, as well as positioning in the respective chamber 17 or 16, the peripheral section 23 and/or the peripheral section 25 is provided with at least one positioning hole 26.

As shown in FIG. 3, the central section 24 is provided with at least one rib or projection 27 which is shown to be substantially V-shaped in cross section, and the peripheral section 23 has a correspondingly cross-sectionally configurated groove or recess 28 which fittingly receives the projection or rib 27 in the assembled condition of the lens body 21. However, it will be appreciated that the location of the projection 27 and recess 28 can be reversed (FIG. 4), or that they could have different, but preferably mutually complementary, cross-sections. An example of such different configurations in shown in FIG. 5, wherein complementary internal and extenral threads 29 and 30 are proved on the sections 23 and 24, respectively. In this instance, ther peripheral section 23 could be constructed merely as a split ring, that is, it could be subtantially, but not completely, circumferentially complete. In this instance, the central section 24 could be threaded into the peripheral section 23, without spreading the latter to any appreciable extent.

FIG. 6 illustrates a modified construction according to the present invention, wherein the lens body 21 consists of three sections, rather than two. In other words, the two peripheral sections 23 and 25 are separate not only from one another, but also from the central section 24. Then, as shown in FIG. 8, male and female formations 31 and 32 are provided on the respective sections 23 and 25 and engage one another with a snap action to hold the sections 23 and 25 together. Such or similar formations 31 and 32 could also be used for connecting the additional peripheral section 25 to the central section 24, instead of or in addition to the positioning and holding arrangements 27 and 28 or 29 and 30.

It will be appreciated that the presence of the various formations or arrangements 28 to 32 and, basically, the multipartite construction of the lens body 21 will result in the presence of irregularities in the lens body 21 due to the presence of the various interfaces and gaps between the sections 23 to 25 thereof. The influence of such irregularities on the quality of the image projected by the lens body 21 in its position of use onto the retina will be minimized by carefully controlling the dimensions and shapes of the sections 23 to 25 such that the sizes of the respective gap or interfaces are kept to a minimum and substantially uniform. Moreover, such gaps and interfaces are situated at a region of the lens body 21 remote from the central axis, where the influence of such irregularities has a much less deleterious effect than if these irregularities were situated at the center of the lens body 21. Also, since the lens body 21 is surrounded by liquid during its use, with the liquid penetrating between the sections 23 to 25 as well, the influence of such irregularities will be further reduced as compared to the situation where air would be present in such interfaces or gaps. Yet, it is still highly desirable not to make such gaps excessively large. This desire, however, runs somewhat contrary to another desire, namely, for the safe construction of the lens body 21 with the sections 23 to 25 within the eye 10. This is why the lens sections 23 to 25 are shown to be rounded at the edges thereof in FIG. 2; yet, the rounding brings about the presence of gaps at the outer periphery of the lens body 21 between the peripheral sections 23 and 25. On the other hand, when the interfaces between the sections 23 and 25 extend along straight, substantially radial, courses, as they do in the construction revealed in FIG. 6, a sharp edge or corner is present at the outer periphery of the end portions of the respective sections 23 and 25. Now, since the peripheral sections 23 must be maneuvered during its introduction into the eye 10 through the reduced-size incision, the presence of the sharp edge at its leading end portion at least is potentially much more deleterious than at any other region of the lens sections 23 to 25. This is why, as shown in FIG. 8, it is further proposed according to the present invention to provide a bulge or bead 33 at least at the leading end portion of the peripheral section 23, but preferably at both of such end portions especially since it can be hardly determined in advance which one of such end portions will be used by the surgeon as the leading end portion. The bead 33 merges with the outer peripheral surface or edge of the peripheral section 23 and gradually deviates therefrom along an arcuate course, until its curvature is reversed, and it gradually merges into the inner peripheral surface of the peripheral section 23. A correspondingly and compatibly, preferably complementarily, configured recess 34 is provided at the corresponding region of the peripheral section 25 for receiving the bulge or bead 33. In the alternative, the surface bounding the bead 33 can be configured as a reentrant curve, as shown in FIG. 9, so that the danger of contact between the eye tissue and any sharp edges of the sections 23 to 25 of the lens body is further reduced.

FIG. 8 also shows the provision of an engaging opening 35 which opens onto the peripheral surface of the lens section 23. This opening 35, which is provided in addition to the positioning openings or holes 26, serves for reception of and engagement by a positioning tool used to manipulate the section 23 in the interior of the eye 10. The opening 35 may have a dove-tailed configuration as shown in FIG. 8, or any other configuration, including conical, cylindrical, cross-sectionally polygonal, especially hexagonal, which is compatible with the configuration of the positioning tool.

During the introduction of the sections 23 to 25 into the eye 10, it may be necessary to provide small additional perforations in the eye tissue for the purpose of passing various positioning tools, which engage in the openings 26 and/or 35 therethrough, to manipulate and eventually assemble the sections 23 to 25 into the lens body 21. However, these additional perforations, which are used in prior art techniques, are relatively small and heal quickly without being sutured.

Having so described the construction of the intraocular lens arrangement or implant 20 of the present invention, its operation will now be briefly discussed, together with discussion of the manner in which the implant 20 is introduced into the eye 10. It will be appreciated that each of the sections 23, 24, and/or 25 has a dimension as considered in the lens plane which is much smaller than the diameter of the lens body 21. So, for instance, the C-shaped peripheral section 23 and/or the additional perhipheral section 25 may have a radial dimension of between 1 and 2 millimeters, preferably 1.25 millimeters, while the diameter of the central section 24 may be between 3 and 4 millimeters, preferably 3.5 millimeters. Hence, the overall diameter of the assembled lens body is somewhere between 5 and 8 millimeters, preferably around 6.0 millimeters. This means that the incision required for the introduction of the lens body 21 in its assembled condition would have to be longer than 6.0 millimeters in the preferred case, while it can be only slightly longer than 3.5 millimeters for the preferred case of sectional lens body of this invention. As current technology allows removal of cataracts by ultrasonically powered hollow needles through a 3.5 millimeter incision, the need for post cataract incision enlargement for the insertion of the implant is obviated. Obviously, the outer diameter of the peripheral section 23 corresponds to that of the lens body 21. Yet, since the peripheral section 23 has a partly annular configuration, it can be snaked into the eye 10 through the relativley small incision as well. Of course, once the lens body 21 is assembled and properly positioned in the eye 10, it will collimate the light rays onto the retina, thus improving vision. The illustrated holding means 22 is only one example of how the implant 20 could be held in position in the interior of the eye 10.

It will be understood that each of the elements described above, or two or more together, may also find a useful application in other types of arrangements differing from the type described above.

While the invention has been illustrated and decribed as embodied in multipartite intraocular lens, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the claims.

What is claimed as new and desired to be protected by Letters Patent is set forth in the appended claims.

I claim:

1. An intraocular lens implant, comprising:
   (a) a lens body centered on a lens axis and extending along a plane normal to said lens axis, said lens body including a plurality of separate sections each of which has at least one dimension as considered along said plane which is a fraction of the diameter of said lens body to permit initial separate introduction of the respective sections into the eyeball through an incision smaller than that which would be needed for the introduction of the complete lens body, followed by subsequent assembly of said sections within the eyeball into the lens body,
   (b) means for holding the assembled lens body in a predetermined position in the eyeball,
   (c) one of said sections being a substantially C-shaped peripheral section and another one of said sections is a substantially circular central section at least partially circumferentially surrounded by said peripheral section in the assembled condition of said lens body,
   (d) said peripheral and central sections having respective internal and external surfaces which face one another in the assembled condition of said lens body, one of said surfaces being provided with at least one projection and the other of said surfaces having at least one recess which receives said projection in the assembled condition of said lens body to hold said central section in a predetermined position relative to said peripheral section, and
   (e) said projection being configured as a substantially circumferentially extending rib, and said recess being configured as a substantially circumferentially extending groove.

2. The intraocular lens implant as defined in claim 1, wherein said lens body further includes an additional peripheral section separate from and substantially complementary to said peripheral section.

3. The intraocular lens implant as defined in claim 21, wherein said additional peripheral section is integral with said central section.

4. The intraocular lens implant as defined in claim 3, wherein said peripheral section has end portions which accommodate said additional peripheral section between themselves, said end portions and said additional peripheral section being provided with substantially complementarily configured locking bulges and depressions which receive said bulges in the assembled condition of said lens body.

5. The intraocular lens implant as defined in claim 4, wherein said bulges are provided on said end portions and said depressions in said additional peripheral section.

6. The intraocular lens implant as defined in claim 5, wherein said bulges are configurated to form a smooth transition at the outer periphery of at last one of said end portions of said peripheral section.

7. The intraocular lens implant as defined in claim 2, wherein said additional peripheral section is separate from said central section and further comprising means for connecting said additional peripheral section to the remainder of said lens body in the assembled condition of the latter.

8. The intraocular lens implant as defined in claim 7, wherein said connecting means includes cooperating male and female connecting portions provided on said sections and engaging one another with a snap action.

9. The intraocular lens implant as defined in claim 1, wherein at leat one of asid sections has an engaging recess which opens on a surface of said one section that constitutes a part of the periphery of said lens body in the assembled condition of the latter, for engagement by a handling tool during the introduction of said one section into the eyeball and/or its assembly with the remainder of said lens body.

10. The intraocular lens implant as defined in claim 9, wherein said engaging recess has a substantially dovetail-shaped configuration.

11. The method of inserting an intraocular lens having a central section, one peripheral section adapted to suround and engage the majority of, but less than all of, the perphery of the central section, and where the diameter of the central section is less than the diameter of the central section and peripheral sections when the aforesaid sections are assembled toegether, comprising the steps of:
   (a) making an incision in the eyeball substantially equal to the diameter of the lens central section,
   (b) inserting the lens central section into the posterior chamber of the eyeball,
   (c) then inserting a peripheral section through the incision,
   (d) positioning the inserted peripheral section adjacent the inserted central section,
   (e) repeating steps (c) and (d) above for each additional peripheral section that is employed, and
   (f) engaging such peripheral section and the central section, and wherein only one peripheral section is employed, and wherein the incision is made on the bias, and wherein one of the central sections and the peripheral section have a V-shaped edge and the other section has a V-shaped groove, and wherein the peripheral section surrounds more than 180 degrees but less than 360 degrees of the periphery of the central section, and further comprising the step of snap fitting the central section into the peripheral section by expanding the peripheral section to permit insertion and engagement of the central section by the peripheral section.

* * * * *